United States Patent [19]
Snowball

[11] Patent Number: 5,951,876
[45] Date of Patent: Sep. 14, 1999

[54] FLUID TREATMENT APPARATUS

[75] Inventor: Malcolm Robert Snowball, Epping, United Kingdom

[73] Assignee: Water Recovery plc, Oxfordshire, United Kingdom

[21] Appl. No.: 08/796,927

[22] Filed: Feb. 7, 1997

Related U.S. Application Data

[63] Continuation-in-part of application No. PCT/GB95/01905, Aug. 11, 1995.

[30] Foreign Application Priority Data

Aug. 11, 1994 [GB] United Kingdom .................... 9416287

[51] Int. Cl.[6] ................................................ B01D 17/06
[52] U.S. Cl. .................. 210/748; 210/791; 210/321.69; 210/333.01; 210/335; 210/340; 210/359; 210/411; 210/433.1; 422/24
[58] Field of Search ................................ 210/333.01, 335, 210/340, 359, 411, 433.1, 500.25, 650, 748, 791, 321.69; 422/22, 24

[56] References Cited

U.S. PATENT DOCUMENTS

| | | |
|---|---|---|
| 2,271,814 | 2/1942 | Coolidge ................................ 210/168 |
| 3,077,989 | 2/1963 | Larkin ................................ 210/340 X |
| 3,326,381 | 6/1967 | Fuller ................................ 210/340 X |
| 3,923,663 | 12/1975 | Reid ................................ 210/251 |
| 4,151,085 | 4/1979 | Malik ................................ 210/101 |
| 4,694,179 | 9/1987 | Lew et al. ................................ 250/431 |
| 4,906,381 | 3/1990 | Barbaro ................................ 210/335 X |
| 4,968,437 | 11/1990 | Noll et al. ................................ 210/748 |
| 4,971,687 | 11/1990 | Anderson ................................ 210/85 |
| 5,213,759 | 5/1993 | Castberg et al. ........................... 422/24 |
| 5,294,339 | 3/1994 | Jorgens ........................... 210/500.25 X |
| 5,330,722 | 7/1994 | Pick et al. ................................ 422/121 |

FOREIGN PATENT DOCUMENTS

| | | |
|---|---|---|
| 3247747 | 8/1983 | Germany . |
| 58-220000 | 12/1983 | Japan . |

*Primary Examiner*—W. L. Walker
*Assistant Examiner*—Terry Cecil
*Attorney, Agent, or Firm*—Edwin D. Schindler

[57] ABSTRACT

A fluid treatment apparatus comprises two titanium mesh filters (12,22) connected in series across a flow passage. Each filter (12,22) is irradiated by UV light from respective lamps (13a,13b,23a,23b), so as to kill any micro-organisms trapped on the filters. Backwashing means (18,19,28,19) are provided for backwashing each filter in succession whilst fluid flowing along the passage is filtered by the other filter. In this manner micro-organisms are unable to pass through the apparatus untreated.

28 Claims, 4 Drawing Sheets

FLUID TREATMENT APPARATUS

CROSS REFERENCE TO RELATED APPLICATION

This application is a continuation-in-part of my International Patent Application PCT/GB95/01905, filed Aug. 11, 1995.

BACKGROUND OF THE INVENTION

1. Field of Invention

This invention relates to fluid treatment apparatus and more particularly, but not solely, to an apparatus for treating drinking water.

2. Description of the Prior Art

Drinking water may be contaminated with foreign matter such as parasites, bacteria, viruses, worms, protozoa, moulds and mould spores, which can be particularly harmful to human beings if ingested. Such foreign matter is often extremely difficult to treat by conventional means, especially if they are resistant to chlorine and other biocides. However some types of foreign matter are susceptible to extremely high doses of ultra-violet radiation.

Conventional ultra-violet fluid treatment apparatus, such as the one disclosed in GB 2175779, comprise an elongate tubular chamber having an axially extending ultra-violet light source. The dose of radiation supplied by the apparatus is equal to the product of the radiation intensity of the light source and the retention time of the fluid inside the chamber. A high fluid flow rate is needed, but it is impractical to increase substantially the radiation intensity of the light.

SUMMARY OF THE INVENTION

We have now devised a fluid treatment apparatus which is able to effectively treat Cryptosporidium and Giardia parasitic micro-organisms and other foreign matter but which can maintain a high fluid flow rate.

In accordance with this invention as seen from a first aspect, there is provided a fluid treatment apparatus comprising a flow passage, a plurality of filter elements mounted across the flow passage for filtering fluid flowing along the passage between an inlet and an outlet of the passage, backwashing means for reversing the flow of fluid through a said filter element whilst fluid flows along the passage between said inlet and outlet through at least one other said filter element, and radiating means for irradiating a surface of the or each said other filter element so as to treat any foreign matter trapped thereon, the backwashing means being arranged to reverse the flow of fluid through each filter element in succession whilst fluid flows along the passage between said inlet and outlet through at least one other said filter element.

In use, any foreign matter that is trapped by the filter is exposed to a continuous dose of radiation, which is sufficiently large to ensure that any living matter is inactivated or killed. Each filter is backwashed in succession, so as to remove any dead or inactivated matter and other debris, which may have built up thereon. At least one filter is arranged across the flow passage during backwashing of another filter, so that untreated matter is unable to pass through the apparatus.

Thus, the flow of fluid does not need to be interrupted in order to perform backwashing.

Preferably the apparatus is arranged such that a predetermined delay occurs between reversing the flow of fluid through adjacent filter elements in the flow passage. This ensures that all of the matter trapped by the filter receives a predetermined amount of radiation, which is preferably greater than the minimum amount of radiation required to inactivate or kill any living matter that it contains. Much of the harmful foreign matter in water is 4–6 microns in diameter, therefore the filter preferably comprises a filter material having pore sizes which are less than 4 microns.

Preferably the radiating means comprises an ultra-violet light source. Preferably the light source radiates short-wave ultra-violet light, preferably having a wavelength of 245–265 nm, and particularly 253.7 nm. Micro-organisms and some other foreign matter are most susceptible to radiation at these wavelengths. Preferably the radiating means irradiates opposite surfaces of the filter.

In one embodiment, the flow passage comprises a pair of chambers each divided into two longitudinally extending portions by respective filters, each portion of each chamber being provided with respective fluid inlet and outlet ports, said backwashing means comprising valves connected to said ports, and control means for selectively opening the inlet port of one portion of each chamber and the outlet port of the other portion of each chamber, so as to cause fluid flow in one direction through both filters. In order to reverse the flow of fluid through the filter the inlet and outlet valves of the opposite portions of each chamber are opened instead. It will be appreciated that fluid continues flow between an inlet and an outlet of the chamber regardless of the direction of fluid flow through the filter.

In an alternative embodiment, the filters are rotatably mounted in the fluid flow passage, said backwashing means comprising an actuator which rotates the filters through 180°, so that fluid flows through them in the reverse direction.

Preferably the filters are arranged in series.

In one embodiment, the filter comprises a mesh formed from a material such as titanium which reacts with water to form an oxide film on its surface. This oxide film reacts with the short-wave UV light to produce hydroxyls in the oxide surface. Foreign matter such as micro-organisms which come into contact with this film are killed or inactivated, owing to the oxidisation of their cell walls.

In an alternative embodiment, the filter comprises a fibrous material which is transparent to radiation emitted by said radiation means.

Preferably the fibrous material comprises PTFE, which is transparent to short-wave UV light.

Also, in accordance with this invention as seen from a second aspect, there is provided a fluid treatment apparatus comprising a flow passage, a filter element mounted across the flow passage for filtering fluid flowing along the passage between an inlet and an outlet of the passage, means for substantially disabling the filtration of the filter, means for irradiating the filter for a predetermined time period after the filtering action of the filter has been disabled, means for backwashing the filter after said time period has ended, and means for enabling the filtering action of the filter following backwashing.

Foreign matter in the fluid, such as micro-organisms, parasites, bacteria, viruses, worms, protozoa, moulds and mould spores can be inactivated or killed by sufficient exposure to radiation from the radiating means. Thus, disabling the filtering action of the filter and then exposing the filter to radiation before backwashing ensures that any foreign matter that has been trapped on the filter is inactivated or killed.

Preferably during backwashing the downstream side of the filter is connected to the outlet, so that bio-hazardous debris which has been removed from the filter does not have to be disposed of.

In one embodiment, the disabling means comprises means for connecting another filter element in front of said filter, so that the filter no longer performs the primary filtering function.

In another embodiment, the disabling means comprises valve means for inhibiting fluid flow between the inlet and outlet.

In some instances the cessation of fluid flow can be tolerated. However, the apparatus preferably comprises reservoir means which stores treated fluid and means for connecting the reservoir to the outlet whilst said fluid flow is inhibited.

In another embodiment, the disabling means comprises means for removing said filter from the flow passage. This can be achieved either by physically moving the filter or by changing the path of the flow passage.

Also, in accordance with this invention as seen from a third aspect, there is provided a method of treating potable water which at least intermittently contains foreign matter by establishing a flow of such potable water from an inlet to an outlet through a filter having openings of 4 micros or less, intercepting the foreign matter on the filter and irradiating the filter with a dose of UV radiation of at least 50 mW Sec/CM$^2$ and then removing the accumulated foreign matter from the filter.

Preferably the filter is backwashed, preferably to the outlet.

Preferably the UV radiation has a wavelength of 245–265 nM.

Embodiments of this invention will now be described by way of examples only, and with reference to the accompanying drawings, in which:

DESCRIPTION OF THE EMBODIMENT SHOWN IN THE FIGURES

Figure 1:
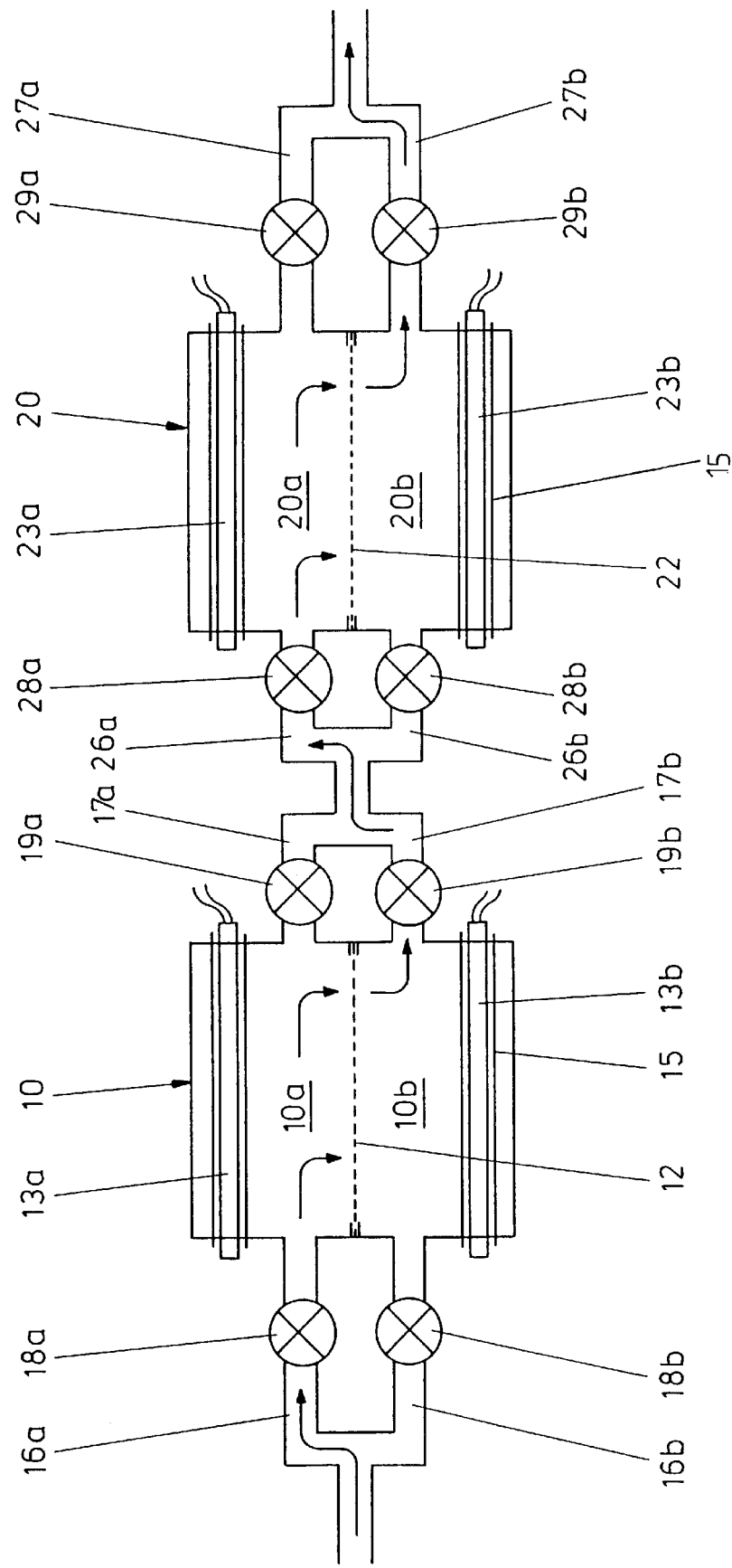
FIG. 1 is a sectional view through a first embodiment of water treatment apparatus in accordance with this invention.

Referring to FIG. 1 of the drawings, there is shown a water treatment apparatus comprising two elongate chambers 10,20 connected in series in a water flow passage. The first chamber 10 comprises upper and lower, longitudinally extending, portion 10a,10b separated by a titanium mesh filter 12. A pair of elongate ultra-violet lamps 13a, 13b extend through the upper and lower portions 10a,10b of the chamber respectively. Each ultra-violet lamp e.g. 13b is mounted inside a quartz glass sleeve 15, which is sealed at its opposite ends to the walls of the chamber.

The upper and lower portions 10a,10b of the chamber are connected at one end to respective branches 16a,16b of an inlet duct, and at the other end to respective branches 17a,17b of an outlet duct. The upper and lower branches of the inlet and outlet ducts 16a, 16b, 17a, 17b are provided with respective fluid flow valves 18a,18b,19a,19b.

The second chamber 20 also comprises upper and lower longitudinally extending portions 20a,20b separated by a titanium mesh filter 22. A pair of elongate ultra-violet lamps 23a,23b extend through the upper and lower portions 20a, 20b of the chamber respectively.

The upper and lower branches 17a,17b of the outlet duct of the first chamber 10 are each connected to upper and lower branches 26a,26b of an inlet duct to the second chamber 20. The upper and lower portions 20a,20b of the second chamber are connected at one end to the respective branches 26a,26b of the inlet duct, and at the other end to respective branches 27a,27b of an outlet duct. The upper and lower branches of the inlet and outlet ducts 26a,26b,27a,27b to the second chamber are provided with respective fluid flow valves 28a,28b,29a,29b.

In use, the valves 18a,19b are opened, such that water flows into the upper portion 10a of the first chamber, through the first filter 12 and into the lower portion 10b of the chamber. The valves 28a,29b are also opened such that water flowing out of the lower portion 10b of chamber flows into the upper portion 20a of the second chamber, through the second filter 22, into the lower portion 20b of the chamber, and out of the apparatus through the outlet duct 27b. Assuming that the ultra-violet lamps 13a,13b,23a,23b are illuminated, then any Cryptosporidium or Giardia micro-organisms in the water will be caught by the first filter 12, and held in front of the radiation from the lamps 13a,13b.

Assuming that the minimum time which the micro-organisms are held in front of the ultra-violet radiation is 5 minutes and that the lamps produce a minimum of 4 mW/cm$^2$ of ultra-violet radiation, then the dose will be:

$$Dose = 4 \times (5 \times 60) = 1200 \text{ mW Sec/cm}^2.$$

It is known that a dose of 50–100 mW Sec/cm$^2$ kills Cryptosporidium and Giardia micro-organisms. Thus, the apparatus in accordance with this invention irradiates the micro-organisms with a dose which is 12 times greater than is needed to kill them. Also, there is very little build up of other debris on the filter, since the apparatus is intended for use in treating clean drinking water.

After 5 minutes the valves 18b,19a are opened, and the valves 18a,19b closed, so that water flows in the reverse direction through the first filter 12, thereby backwashing the filter. Any debris and micro-organisms caught by the first filer 12 are washed through onto the second filter 22, where they receive a further dose of radiation. After 5 more minutes the valves 28b,29a are opened, and the valves 28a,29b closed, so that water now flows in the reverse direction through the second filter.

All the harmful micro-organisms on the second filter 22 have been killed, and thus the second filter can be safely backwashed into the flow stream out of the apparatus.

This process continues, so that the direction of flow through each filter 12,22 is reversed every 10 minutes, with a 5 minute interval between successive reversals, so that all micro-organisms caught by the apparatus are exposed to radiation for at least 5 minutes.

Figure 2:
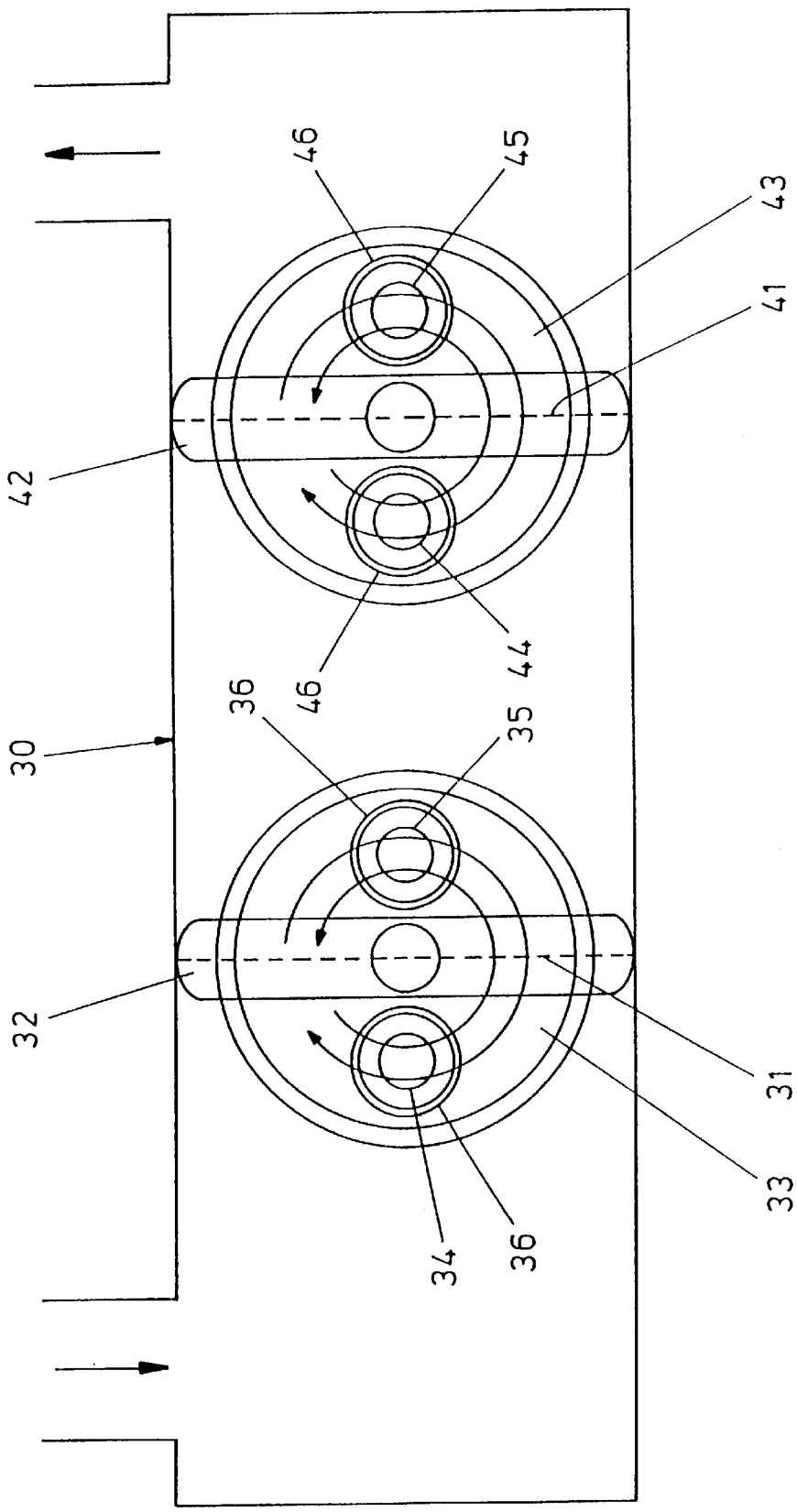
FIG. 2 is a sectional view through a second embodiment of water treatment apparatus in accordance with this invention.

Referring to FIG. 2 of the drawings, there is shown a second embodiment of water treatment apparatus comprising an elongate tubular chamber 30 connected in series with a water flow passage. A circular titanium mesh filter 31, having an annular seal 32 around its periphery, is mounted normal to the direction of fluid flow, such that all of the water flowing through the apparatus is filtered. The filter 31 is mounted on a rotatable carrier 33, which also carries a pair of tubular ultra-violet lamps 34,35 mounted inside quartz glass sleeves 36. The lamps 34,35 are arranged to illuminate opposite sides of the filter 31.

A second titanium mesh filter 41, having an annular seal 42 around its periphery, is mounted downstream of the first filter 31. The second filter 41 is mounted on another rotatable carrier 43, which also carries a pair of tubular ultra-violet lamps 44,45 mounted inside quartz glass sleeves 46.

In use, micro-organisms are trapped by the filter 31, which is mounted across the flow passage. The ultra-violet lamps 34,35 illuminate the filter. After 5 minutes the carrier 33 is rotated through 180°, so that water now flows in the reverse direction through the filter 31, thereby backwashing the filter. Any debris and micro-organisms caught by the first filter 31 are washed through onto the second filter 41, where they receive a further dose of radiation from the lamps 44,45. After 5 more minutes the carrier 43 is rotated, so that water now flows in the reverse direction through the second filter 41.

As before, all the harmful micro-organisms which have collected on the filter 41 are killed by the ultra-violet radiation, and thus the debris from the second filter can be safely backwashed into the flow out of the apparatus.

Each filter is rotated through 180° every 10 minutes, with a 5 minute interval between successive rotations, so that all of the micro-organisms caught by the filter are exposed to radiation for at least 5 minutes.

Figure 3:
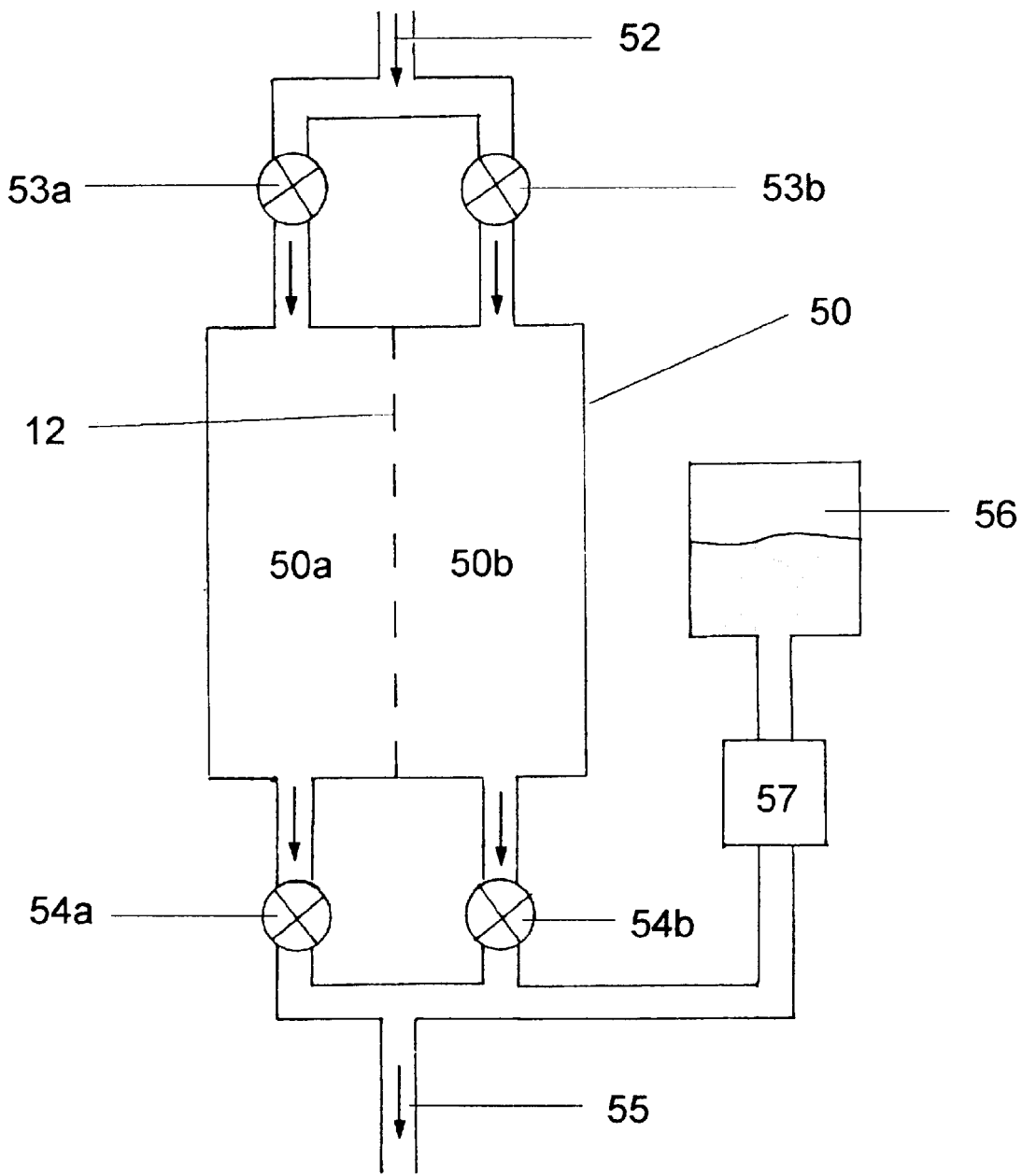
FIG. 3 is a schematic diagram of a third embodiment of water treatment apparatus in accordance with this invention.

Referring to FIG. 3 of the drawings, there is shown a third embodiment of water treatment apparatus comprising a single chamber 50, which is divided into two portions 50a, 50b by a filter 12. A pair of ultra violet lamps (not shown) extend through respective portions of the chamber for irradiating opposite sides of the filter 12.

The upper end of both portions 50a,50b of the chamber 50 are connected to an inlet 52 by respective inlet valves 53a, 53b. Likewise, the lower end of both portions 50a,50b of the chamber 50 are connected to an outlet 55 by respective outlet valves 54a,54b. The outlet 55 is also connected to a reservoir tank 56 via a pump 57.

In use, the valves 53a,54b are opened, such that water flows from inlet 52 to outlet 55 through the filter. Treated water also fills the reservoir 56. At least the upstream side of the filter 12 is irradiated by UV light to kill or inhibit any micro-organisms trapped thereon.

The valves 53a,54b are closed after a predetermined time, so that no water flows through the chamber 50 However, the demand for water is met by pumping treated water from the reservoir 56 to the outlet 55.

The values 53,54 remain closed for at least 5 minutes, which is the minimum exposure time for ensuring that all of the trapped micro-organisms have been safely treated by the UV light. The reservoir preferably has a capacity which is sufficient enough to meet demand for 5 minutes.

After 5 minutes, the valves 53b,54a are opened, such that water now flows from the inlet 52 to outlet 55 in the reverse direction through filter 12. This backwashes the filter 12, such that the treated foreign matter is washed through to the outlet 55. The process then repeats itself after the reservoir has re-filled from the outlet 55.

In an alternative embodiment, e.g. for home use, it may be acceptable to have a period of no supply, and thus the reservoir may be omitted. The period of no supply may be arranged to coincide with a period of no demand, and for this purpose a pressure sensor may be located at the outlet 55.

Figure 4:
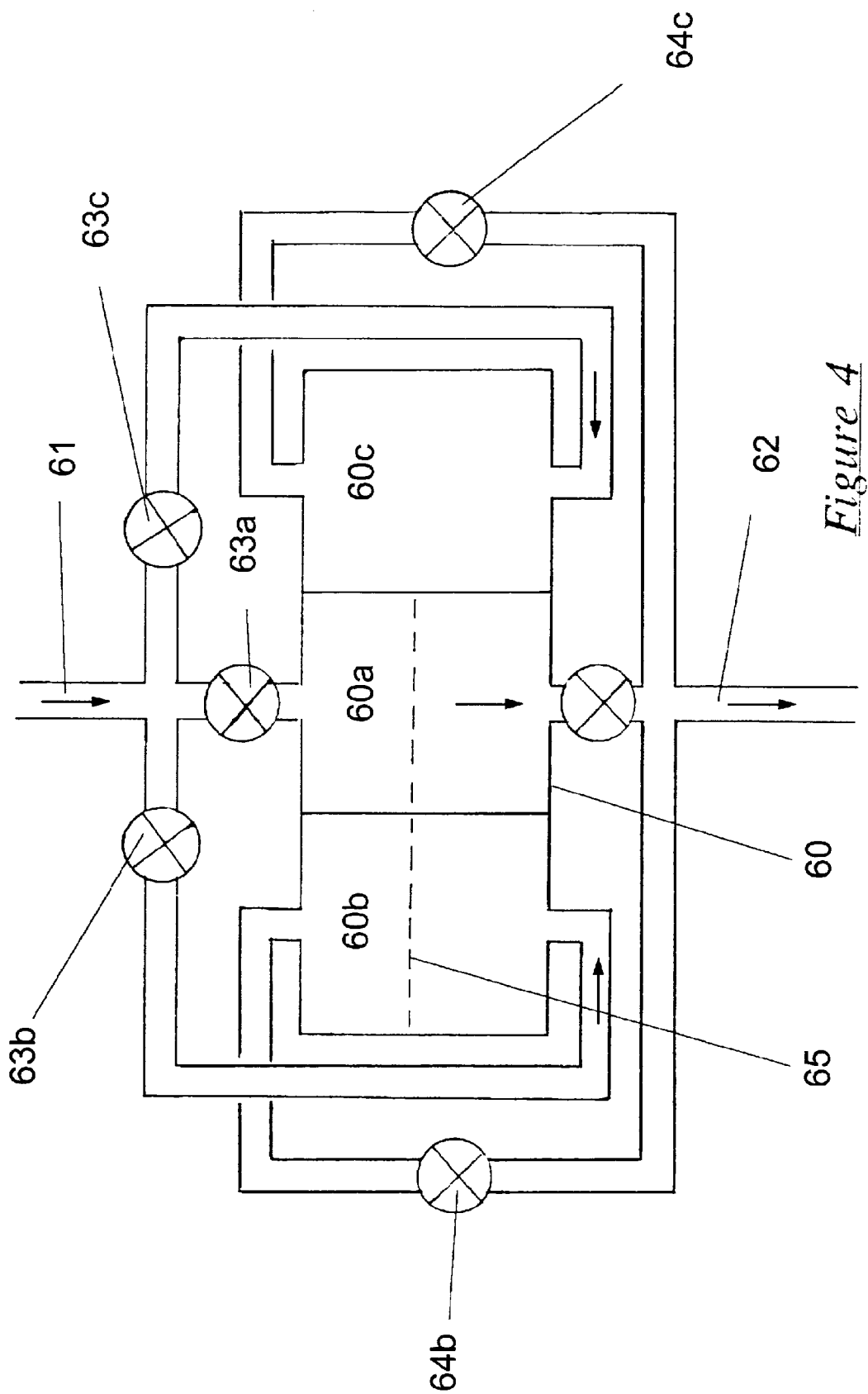
FIG. 4 is a schematic diagram of a fourth embodiment of water treatment apparatus in accordance with this invention.

Referring to FIG. 4 of the drawings, there is shown a fourth embodiment of water treatment apparatus comprising a single chamber 60, which is divided into a central and two outer portions 60a,60b,60c by internal dividing walls.

A filter 65 is slidably mounted inside the chamber 60, perpendicular to the dividing walls. In one position the filter 65 extends across the central and one outer portion 60a,60b of the chamber, and in another position the filter 65 extends across the central and the other outer portion 60a,60c of the chamber. The filter 65 may comprise a single filter, alternatively it may comprise two separate filters mounted side-by-side.

The filter 65 is able to divide each portion 60a,60b,60c of the chamber into an upper and a lower part. The upper and lower parts of the central portion 60a of the chamber are respectively connected to an inlet 61 and outlet 62 by respective valves 63a,64a.

The upper and lower parts of the outer portions 60b,60c of the chamber are respectively connected to the outlet 62 and inlet 61 by respective valves 64b,64c,63b,63c.

In use, all valves are closed and the filter 65 is slid to the position shown in FIG. 4. Next, the valves 63a, 64a are opened, so that water can flow from inlet 61 to outlet 62 through the right hand part of the filter 65 in the central portion 60a of the chamber. A UV lamp irradiates the upstream side of the filter 65 in the central portion 60a of the chamber.

After a while, the filter 65 is ready for backwashing, and in order to do this an actuator moves the filter 65 to the right as water continues to flow through the central portion 60a of the chamber.

The contaminated right hand part of the filter is now located in the outer portion 60c of the chamber, where it is irradiated for at least 5 minutes by a UV lamp (not shown).

After 5 minutes the valves 63c,64c are opened and water now flows in the reverse direction through the previously contaminated right hand part of the filter disposed in the outer portion 60c of the chamber, thereby backwashing the filter. The debris from the filter flows to the outlet 62.

Debris now collects on the underside of the right hand part of the filter in 60c. Thus, in order to deal with this, the valves 63c,64c are closed so that water now only flows through the central portion 60a of the chamber. The underside of the right hand part of the filter 65 in 60c is exposed to UV radiation from a lamp (not shown) for at least 5 minutes, whereupon the filter is moved to the left, so that the flow through the central portion 60a backwashes the debris from the underside of the filter.

The left hand part of the filter, which is contaminated, is now located in 60b, where it is irradiated for at least 5 minutes by a UV lamp (not shown).

After 5 minutes, the valves 63b,64b are opened and water flows in the reverse direction through the previously contaminated left hand part of the filter disposed in the outer portion 60b of the chamber, thereby backwashing the filter. The debris from the filter flows to the outlet 62.

Debris now collects on the underside of the left hand part of the filter 65 in 60b. Thus in order to deal with this, the valves 63b,64d are closed so that water now only flows through the central portion 60a of the chamber. The underside of the left hand part of the filter 65 in 60b is exposed to UV radiation from a lamp (not shown) for at least 5 minutes, whereupon the filter 65 is moved back to the left, so that the flow through the filter backwashes the debris from the underside of the filter 65.

The right hand part of the filter, which is contaminated, is again located in 60c, and the process thus repeats itself.

It will be appreciated that the valves 63a,64a can be omitted.

It will be appreciated that each embodiment of the invention delivers a dose of radiation to all of the trapped micro-organisms (and other foreign matter), which is at least 12 times greater than is necessary to kill them. The mesh filters used do not significantly affect the water flow rate, so that there is little resulting loss in water pressure at the consumer. The effectiveness of the system can be increased by providing more than two filters or more than one filtration stage.

Each of the apparatus described herein are particularly suited to treating micro-organisms, such a cryptosporidium and giardia (which are particularly harmful to humans, and which are commonly found in water). However, it will be appreciated that the apparatus could also treat other foreign matter or contaminants in the water, such as parasites, bacteria, viruses, worms, protozoa, moulds and mould spores.

In some instances these other foreign bodies may be susceptible to the same type of radiation as is suitable for treating cryptosporidium and giardia. However it is envisaged that the apparatus could emit different radiation in addition to or instead of the UV radiation emitted by the apparatus shown in the drawings, depending on the type of foreign mater that is found in the fluid being treated.

I claim:

1. A fluid treatment apparatus comprising a flow passage, a filter element mounted across the flow passage for filtering fluid flowing along the passage between an inlet and an outlet of the passage, means for substantially disabling the filtration of the filter, means for irradiating the filter for a predetermined time period after the filtering action of the filter has been disabled, means for backwashing the filter after said time period has ended, and means for enabling the filtering action of the filter following backwashing.

2. A fluid treatment apparatus as claimed in claim 1, in which the disabling means comprises means for connecting another filter element upstream of said filter.

3. A fluid treatment apparatus as claimed in claim 2, further comprising means for backwashing said other filter in the flow passage upstream of said filter, once said filter enabling means has enabled the filtering action of said filter.

4. A fluid treatment apparatus as claimed in claim 3, wherein the flow passage comprises upstream and downstream chambers connected in series and divided into two longitudinally extending portions by said upstream and said filter respectively, each portion of each chamber being provided with respective fluid inlet and outlet ports, said backwashing means comprising valves connected to said ports and control means for selectively opening the inlet ports of one portion of each of said chambers and the outlet ports of the other portions of respective said chambers.

5. A fluid treatment apparatus as claimed in claim 3, wherein said filters are rotatably mounted in the fluid flow passage, said backwashing means comprising actuators which rotate the filters through 180° in said flow passage.

6. A fluid treatment apparatus as claimed in claim 2, further comprising means for irradiating said another filter.

7. A fluid treatment apparatus as claimed in claim 1, in which the disabling means comprises means for removing said filter from the flow passage.

8. A fluid treatment apparatus as claimed in claim 7, in which the removing means comprises an actuator which displaces the filter.

9. A fluid treatment apparatus as claimed in claim 7, in which the removing means comprises means for diverting the flow passage through another filter.

10. A fluid treatment apparatus as claimed in claim 1, wherein said irradiating means comprises an ultraviolet light source.

11. A fluid treatment apparatus as claimed in claim 10, wherein said ultraviolet light source irradiates light having a wavelength of 245–265 nM.

12. A fluid treatment apparatus as claimed in claim 11, wherein said ultraviolet light source irradiates light having a wavelength of 253.7 nM.

13. A fluid treatment apparatus as claimed in claim 1, in which the disabling means comprises valve means for inhibiting fluid flow between the inlet and outlet.

14. A fluid treatment apparatus as claimed in claim 13, comprising reservoir means for storing treated fluid and means for connecting the reservoir to the outlet whilst said fluid flow is inhibited.

15. A fluid treatment apparatus as claimed in claim 1, in which the backwashing means is arranged to connect the downstream side of the filter to the outlet during backwashing.

16. A fluid treatment apparatus as claimed in claim 1, wherein said filter disabling means periodically disables the filter, said irradiating means irradiating the filter for a predetermined time period during each successive period that the filtering action of the filter is disabled, said backwashing means backwashing the filter after each predetermined time period has ended, prior to the filtering action of the filter being enabled.

17. A method of treating fluid comprising the steps of establishing a fluid flow along a flow passage through a filter disposed between an inlet and an outlet of the flow passage, substantially disabling further filtration by said filter, exposing the filter to radiation for a predetermined time period after filtration is disabled, backwashing the filter after said predetermined time period has ended, and subsequently enabling the filter, so that filtration continues.

18. A method as claimed in claim 17, in which another filter is connected upstream of said filter in order to substantially disable the filtration by the latter filter.

19. A method as claimed in claim 18, further comprising the step of irradiating the another filter.

20. A method as claimed in claim 18, further comprising the step of backwashing said other filter in the flow passage upstream of said filter, once the filtering action of said filter has been enabled.

21. A method as claimed in claim 17, in which the filter is disabled by removing it from said flow passage.

22. A method as claimed in claim 21, in which the filter is displaced from said flow passage.

23. A method as claimed in claim 21, comprising connecting a by-pass flow passage across said filter and establishing a fluid flow through a filter in said by-pass flow passage.

24. A method as claimed in claim 17, in which the filter is disabled by closing said flow passage to fluid flow.

25. A method as claimed in claim 24, comprising connecting a reservoir of treated fluid to said outlet whilst said flow passage is closed.

26. A method as claimed in claim 17, in which the filter is irradiated during filtration.

27. A method as claimed in claim 17, in which the filter is backwashed to said outlet.

28. A method as claimed in claim 17, further comprising the steps of periodically disabling the filtering action of the filter, irradiating the filter for a predetermined time period during each successive period that the filtering action of the filter is disabled, backwashing the filter after each predetermined time period has ended, prior to enabling the filtering action of the filter.

* * * * *